US012574648B2

(12) United States Patent
Le Clément De Saint-Marcq et al.

(10) Patent No.: US 12,574,648 B2
(45) Date of Patent: Mar. 10, 2026

(54) MULTI-CAMERA HEAD-MOUNTED DEVICE

(71) Applicant: IRISTICK NV, Sint-Martens-Latem (BE)

(72) Inventors: Vianney Le Clément De Saint-Marcq, Sint-Martens-Latem (BE); Riemer Grootjans, Sint-Martens-Latem (BE); Jasper Van Bourgognie, Sint-Martens-Latem (BE); Peter Verstraeten, Sint-Martens-Latem (BE)

(73) Assignee: IRISTICK NV, Sint-Martens-Latem (BE)

( * ) Notice: Subject to any disclaimer, the term of this patent is extended or adjusted under 35 U.S.C. 154(b) by 266 days.

(21) Appl. No.: 18/252,569

(22) PCT Filed: Nov. 10, 2021

(86) PCT No.: PCT/EP2021/081284
§ 371 (c)(1),
(2) Date: May 11, 2023

(87) PCT Pub. No.: WO2022/101289
PCT Pub. Date: May 19, 2022

(65) Prior Publication Data
US 2024/0022823 A1 Jan. 18, 2024

(30) Foreign Application Priority Data

Nov. 12, 2020 (EP) .................................... 20207240

(51) Int. Cl.
*H04N 23/698* (2023.01)
*A61B 90/00* (2016.01)
(Continued)

(52) U.S. Cl.
CPC ......... *H04N 23/698* (2023.01); *A61B 90/361* (2016.02); *G03B 37/04* (2013.01);
(Continued)

(58) Field of Classification Search
CPC ...... G02B 2027/0138; G02B 2027/014; G02B 27/017; G02B 2027/0178; G02B 27/01; G02B 23/125; H04N 23/45; H04N 23/57; H04N 23/698; H04N 23/90; G05B 2219/23148
(Continued)

(56) References Cited

U.S. PATENT DOCUMENTS 8,965,460 B1 2/2015 Rao et al.
9,736,368 B2 8/2017 Lablans
(Continued)

FOREIGN PATENT DOCUMENTS

EP 3467585 A1 4/2019

OTHER PUBLICATIONS

ISR-WO dated Feb. 9, 2022 for parent matter PCT/EP2021/081284.

*Primary Examiner* — Nathnael Aynalem
(74) *Attorney, Agent, or Firm* — Vorys, Sater, Seymour and Pease LLP

(57) ABSTRACT

The current invention relates to a multi-camera head-mounted device. The device may be in the form of a headset, smart glasses, a modular device which can be attached to another headset or other headwear (such as a hard hat, a cap, headband, or others).

17 Claims, 5 Drawing Sheets

(51) Int. Cl.

| | |
|---|---|
| *A61B 90/50* | (2016.01) |
| *G03B 37/04* | (2021.01) |
| *H04N 23/57* | (2023.01) |
| *H04N 23/667* | (2023.01) |
| *H04N 23/90* | (2023.01) |

(52) U.S. Cl.
CPC ........... *H04N 23/57* (2023.01); *H04N 23/667* (2023.01); *H04N 23/90* (2023.01); *A61B 2090/371* (2016.02); *A61B 2090/502* (2016.02)

(58) Field of Classification Search
USPC ................................................. 348/48; 345/8
See application file for complete search history.

(56) References Cited

U.S. PATENT DOCUMENTS

| | | | | |
|---|---|---|---|---|
| 10,013,763 | B1* | 7/2018 | Brailovskiy | ......... H04N 23/698 |
| 10,477,157 | B1 | 11/2019 | Shahdi et al. | |
| 10,567,641 | B1 | 2/2020 | Rueckner | |
| 2017/0363885 | A1 | 12/2017 | Blum et al. | |
| 2018/0348529 | A1* | 12/2018 | Blum | ................ G02B 27/0172 |
| 2019/0114797 | A1* | 4/2019 | Bleyer | ................... G06T 7/579 |
| 2019/0364223 | A1* | 11/2019 | Masuda | ................ H04N 23/00 |

* cited by examiner

MULTI-CAMERA HEAD-MOUNTED DEVICE

FIELD OF THE INVENTION

The present invention relates to a multi-camera head-mounted device. The device may be in the form of a headset, smart glasses, a modular device which can be attached to another headset or other headwear (such as a helmet, hard hat, a cap, headband, or others).

BACKGROUND

In many situations, an operator using a HMD with inbuilt camera is limited by the position and orientation of the camera. In some cases, it is relevant for the operator to have a camera facing forward, while he is facing downward himself, or the other way around. Particular situations in which this is useful is in order-picking, surgery and remote assistance, where the focus point of the user's vision does not always overlap with the desired field of view of the camera.

In some cases, this is solved by providing a tiltable camera, which can be manually adjusted in order to achieve the desired field of view for the camera. However, this requires a hinged connection between camera and HMD, which constitutes a weak point mechanically speaking, and furthermore requires an electronically challenging burden for the data and power supply, which have to accommodate the flexibility of the camera. Furthermore, in order to achieve such a tiltable camera, this will require a mechanical construction which is unfit to be used at the center of the HMD. This means that there will be an undesirable offset in view of the operator's own vision. While in some cases this may not be an issue, in others, such as surgery, this is not allowable. Furthermore, in some cases, a manual adjustment in the middle of another procedure (again, referring to a surgery) is not possible due to hygienic reasons or other reasons. Lastly, the solution still faces the problem that only a single field of view can be picked, requiring that a choice must always be made. For certain applications where the operator himself wearing the device is the only one interacting, this may prove surmountable, but in cases of remote assistance, multiple points of view are often necessary, amongst which foremost the field of view matching or approximating the vision of the operator wearing the device.

Multi-camera HMD's are known in the prior art, but relate to a wider field of view (and sometimes in order to have a rear view). Such devices employ a number of imagers positioned around the head, each oriented slightly more outward, in order to achieve a landscape view on the surroundings. A document describing such a configuration is U.S. Pat. No. 8,965,460, wherein the multiple cameras can be used simultaneously to provide a 360° experience.

EP 3,467,585 describes a VR head-mounted device with a number of cameras. The cameras are positioned at the edges of the HMD, towards the lateral sides and are facing outwards, and are not aligned in a vertical plane substantially parallel to the sagittal plane, except for the bottom two cameras, which are parallel and overlap. EP '585 intends to provide for as large a field of view as possible, but does not address the current issue, namely providing for a maximized vertical image, which is processed in the correct orientation. EP '585 does not have two imagers with a field of view in parallel vertical planes, where one faces upwards and the other downwards in view of a transverse plane. Additionally, the imagers of EP '585 are spaced out significantly to maximize the combined field of view. It does not allow for an easy combination of the images into a single image that represents a vertically extending field of view. Lastly, it is impossible to wear the HMD of EP '585 in two different, inverted modes, nor is there mention of adapted processing when in one of said modes.

U.S. Pat. No. 10,477,157 describes a head-worn sensor array, for VR or AR applications. The device has two separate imagers, each again facing outwardly, but in the same horizontal plane (when the user is standing upright and facing forward with their head straight). There is no possibility to wear the device in two different, inverted modes, nor are there provisions for adapted processing when in one of said modes.

U.S. Pat. No. 10,567,641 describes a head-mounted device with a plurality of imagers positioned over the device's circumference. However, the field of view is centered in a single (horizontal) plane for each imager.

It is clear that none of the known systems are able to overcome the presented issues, and that an improved HMD system is necessary.

SUMMARY OF THE INVENTION

The present invention and embodiments thereof serve to provide a solution to one or more of above-mentioned disadvantages, as well as other issues identified in what follows, or which can be derived from the state of the art in view of the present invention.

The invention relates to a head-mounted device (HMD) comprising at least two spatially separated imagers. The HMD comprises a front side and a back side, a top side and a bottom side divided by a transverse plane, and two lateral sides divided by a sagittal plane. When the HMD is worn by a forward facing user, said transverse plane is essentially horizontal and said sagittal plane is essentially vertical and perpendicular to the transverse plane. It should be noted that the above sides merely refer to a frame of reference for the HMD, and one or more of said sides may or may not be an actual face (flat or curved) of the HMD.

The imagers are oriented under a different polar angle, said polar angle being the angle of the perpendicular projection of the orientation of the imagers onto the sagittal plane with respect to the transverse plane. It can be understood that the polar angle of the vision orientation of a user facing straight forward would be 0°.

The imagers are oriented under a substantially similar azimuthal angle, the azimuthal angle of the imagers being the angle of the perpendicular projection of the orientation of the imagers onto the transverse plane with respect to the sagittal plane, preferably whereby said azimuthal angles are between −15° and +15°, more preferably between −5° and +5°, most preferably about 0°. For a forward facing user, the azimuthal angle of the vision orientation would be about 0°, and so strongly corresponds to the azimuthal angle of the imagers.

The orientations of the first imager and the second imager define an angle of at least 15°, preferably at least 25°, more preferably at least 30°, more preferably at least 35° therebetween, allowing the imagers to augment each other's field of view.

The orientations of the first imager and the second imager extend into different half spaces defined by the transverse plane. This can be understood, again when the HMD is worn by a user facing forward with the transverse plane of the HMD being parallel to the horizontal plane, as one imager being tilted upwards, and the other downwards.

The field of view of the imagers is partially but not entirely overlapping, preferably whereby at most 70%, more preferably at most 50%, of the aggregated field of view of the two imagers being an overlapping field of view of the imagers.

Preferably the overlapping field of view has an angle of at least 20°, preferably at least 25°, more preferably at least 30° in the sagittal plane originating from a center point between the imagers, and even preferably at least 35°, and most preferably at least 40°.

The HMD is adapted to be worn in a first mode with the top side facing up and the bottom side facing down, and in a second mode with the top side facing down and the bottom side facing up, wherein the HMD comprises an orientation determination means, preferably a gyroscope and/or an accelerometer and/or a magnetometer, for determining whether the HMD is worn in the first or second mode, thereby determining the orientation of the first and second imagers. It should be pointed out that in some embodiments, use can be made of a memory of the orientation determination means, wherein a temporary reversal of the HMD (for instance, when bending over with the head downwards) could be ignored if not lasting longer than a predetermined time. Alternatively, this can also be accomplished via recognition of a way the HMD is attached to a carrier, mechanically or electronically.

Based on said determined mode wherein the HMD is worn and/or the orientation, the images are processed (on the HMD and/or on an external device) in a first processing mode or in a second processing mode. Said processing modes take into account the orientation of the HMD/imagers to more efficiently process the images.

In a second aspect, the HMD comprises a longitudinal front frame for being worn at the forehead and eyes of a user, said front frame comprising at least two spatially separated imagers each with a substantially oblong rectangular field of view, said imagers both facing forward, away from a user wearing the HMD; said front frame further comprising one or more displays visible to the user when being worn; wherein the imagers are oriented under a different polar angle, the polar angle of the imagers being the angle of the orientation of the imagers in the plane perpendicular to the longitudinal axis of the front frame with respect to an axis extending away from a user wearing the HMD from the front frame, with the second imager pointing downward with respect to the first imager when the HMD is worn by forward facing user, wherein the field of view of the imagers is partially but not entirely overlapping, preferably whereby at most 70%, more preferably at most 50%, of the aggregated field of view of the two imagers being an overlapping field of view of the imagers; and wherein the imagers are oriented under a substantially similar azimuthal angle, the azimuthal angle of the imagers being the angle of the orientation of the imagers in a plane which encompasses the longitudinal axis of the front frame with respect to the axis extending away from a user wearing the HMD from the front frame, preferably where the overlapping field of view originating from the front frame has an angle of at least 40° in the plane perpendicular to the longitudinal axis of the front frame; and wherein the display is configured for displaying images from the first imager, images from the second imager or aggregated images from the first and second imagers, wherein said aggregated images are created by combining images from the first and second imager into a single, aggregated image.

It is clear from the above aspects that the invention involves an HMD or HMD-modular device (i.e., attachable to a carrier that can be worn on the head, together forming an HMD), where the first and second imagers are positioned in a way that ensures that—under normal use (with the user wearing the device or carrier as logic dictates, and standing up straight, facing forwards with their head straight)—the imagers are oriented in parallel vertical planes, but with one facing more upwards than the other. Typically, HMD devices comprise a longitudinal shape that, when worn, stretches across the forehead, eyes, brow, etc., horizontally, with the imagers clustered close together (within 5.0 cm, preferably within 4.0 cm, 3.0 cm or even closer, such as 2.0 cm), usually central, and oriented with their field of view centered around an axis in the plane perpendicular to the longitudinal axis of the HMD. This plane typically corresponds to the sagittal plane of the user. We note that this is also the usual plane in which the vision of the user is centered. As such, by then taking into account the fact that one imager faces upwards in view of a transverse plane through the HMD, and one faces downwards in view thereof, the combined images show a long, vertically extending field of view that is centered around the sagittal plane.

It should be noted that the orientation and general angulation and position of the components of the HMD can also be inferred from the figures. Of course, these represent specific embodiments, but the general principles regarding orientation, as discussed above, can be understood clearly therefrom.

In a specifically preferred embodiment, the imagers are positioned within 5.0 cm, or even 4.0 cm or 3.0 cm, from each other, with minimized lateral spacing to ensure that—when the user is holding his head straight—the images from both imagers are centered on an almost identical vertical axis. This is especially convenient since one of the goals is to provide for a combined image which suffers from strongly reduced parallax and other negative effects, allowing easy recombination. The minimized lateral spacing is usually translated in the two imagers being directly below or above each other. However, in some more compact embodiments, this may be impossible due to size constraints, resulting in a side-along or diagonal position of the two imagers. Nonetheless, the lateral spacing is reduced to a maximal distance of 4.0 cm, preferably below 3.0 cm and even below 2.0 cm. The vertical distance between the two is of lesser concern as long as there is overlap of the field of view. A higher vertical distance may result in a blind spot extremely close to the HMD, but this region is usually inconsequential, and it can be minimized easily, for instance by having the topmost imager facing downwards, and the bottom imager facing upwards.

In a further aspect, the invention relates to the use of the head-mounted device according to the first aspect (or according to the second aspect) of the invention, during surgical procedures.

Alternatively, the invention relates to the use of the head-mounted device according to the first aspect of the invention, in order-picking. Additionally, the invention relates to the use of the head-mounted device according to the first aspect of the invention, during remote assistance.

DETAILED DESCRIPTION OF THE INVENTION

Figures 1A, 1B:
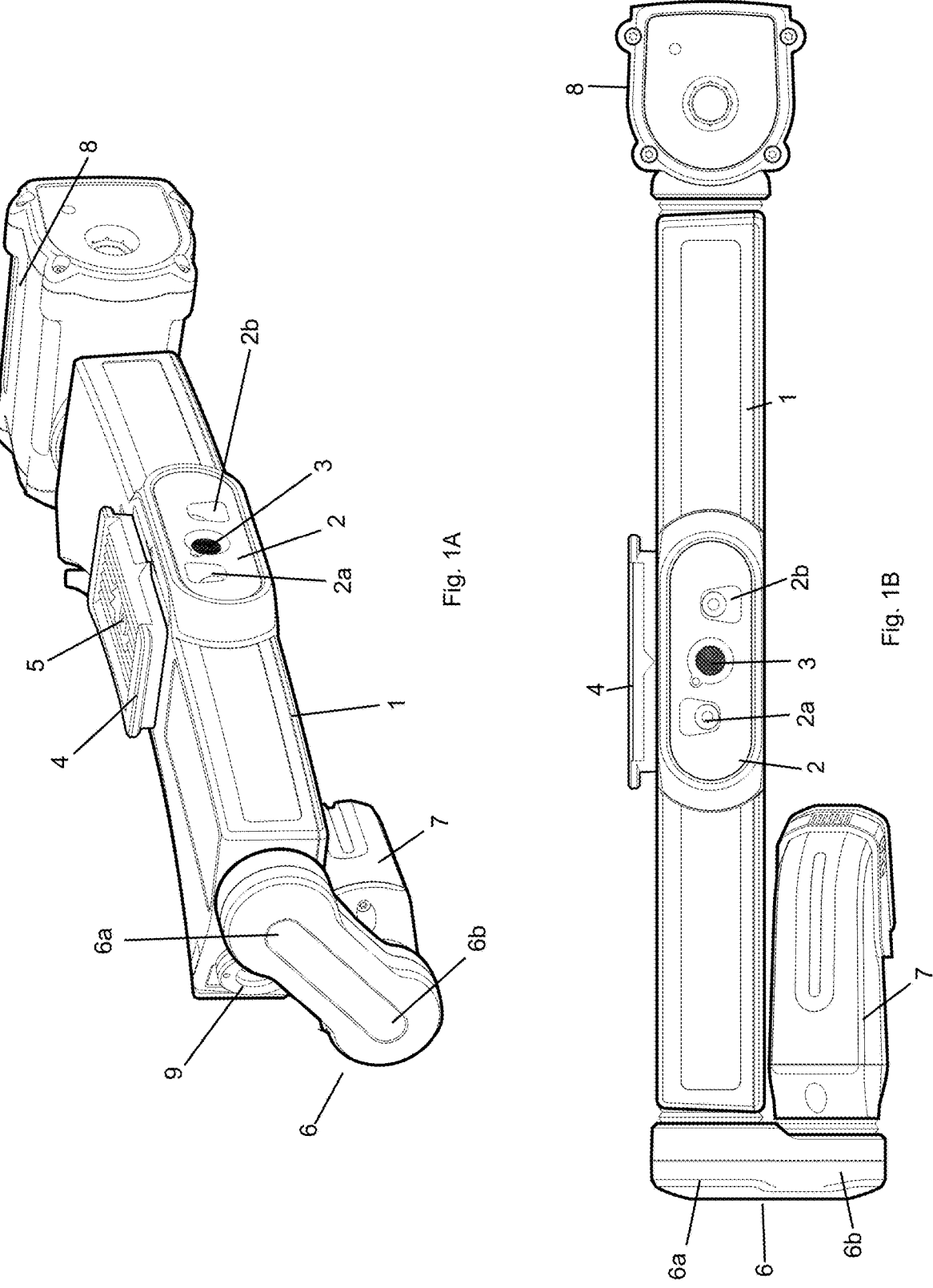
FIG. 1A-B show a perspective view of a HMD according to an embodiment of the invention, without (1A) and with (16) a connection means attached to the HMD.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

In the context of this document, the expressions "forward", "front", "backward", "back" are to be interpreted in terms of the device being worn by a person standing up and facing straight ahead. The terms "vertical" and "horizontal" are to be understood in a similar point of view.

The term "sagittal plane" refers to a fictional plane separating the two lateral sides of the HMD. When used normally (i.e. by a forward facing user standing up straight), the sagittal plane of the HMD corresponds to that of the user, and is essentially vertical, extending along the line of sight of the user.

In the case of the HMD, the sagittal plane furthermore can be defined as a plane to which (the averaged line of sight of) the imagers are each oriented parallel.

The term "transverse plane" refers to a fictional plane separating the top and bottom side of the HMD. When used normally (i.e. by a forward facing user standing up straight), the transverse plane of the HMD corresponds to that of the user, and is essentially horizontal, extending along the line of sight of the user.

"Azimuthal angle" of a certain direction/orientation as used herein, refers to the angle between a perpendicular projection of the certain direction/orientation onto the transverse plane and the sagittal plane. This can also be considered as the angle between said perpendicular projection and a reference axis which lies in the transverse/horizontal plane and is perpendicular to the HMD, facing away from the user (said reference axis can be considered to be equivalent to an axis extending straight ahead from a person standing up straight).

"Polar angle" of a certain direction/orientation as used herein, refers to the angle between the transverse plane and the perpendicular projection of the orientation of the imagers onto the sagittal plane, or alternatively, to the angle between the direction/orientation and a perpendicular projection of said direction/orientation onto the transverse plane.

"Orientation" of an imager refers to the vector of the averaged line of sight of the imager.

The term "processing" is meant to reflect the entire process between capturing the images and the images being displayed. As such, processing may comprise reading out image data from imagers, manipulating the image data, up to the point of determining the fashion in which the image data is displayed.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In a first aspect, the invention relates to a head-mounted device (HMD) according to claim 1. Determining the orientation can be achieved in a number of ways, either via directly determining said orientation (tilt) via one of the aforementioned means, such as an inclinometer, or indirectly, by determining the relative vertical position of the two imagers (which one is positioned above or below other one), which, combined with the known (relative) orientation of the two imagers with respect to each other or the HMD, leads to the determination of the orientation of the two imagers with respect to each other in the overall reference frame. The latter option can also be accomplished by determining the mode wherein the HMD is worn (i.e., which side is facing up).

The term "orientation" in this sense does not require the determination of the exact angle with respect to a known reference frame. In the present case, it is sufficient to know which imager faces more upwardly than the other imager. As such, it can be understood to be an absolute relative angle of the two imagers, which only needs to establish which imager is tilted more (or less) upwardly with respect to the horizontal plane than the other imager.

The present invention provides for a number of advantages over the prior art, and solves a slew of issues present therein. Firstly, it should be noted that a tiltable imager, allowing the imager to be rotated upwards and downwards, has a number of downsides, making it undesirable, impractical and inappropriate or even unallowable in certain situations (surgery). As such, the issue cannot be sufficiently addressed by providing a tiltable imager. Furthermore, in some cases, it is necessary to obtain visuals from separate locations which are distanced too far. For instance, a remote operator may have multiple screens through which he can display multiple images or different sections, which is impossible if the required areas of attention cannot be secured at once.

In order to address the issues, a second imager is provided on the HMD, with both imagers (preferably oriented in portrait mode) and sufficiently proximate to each other to allow proper combination of the two images (reducing parallax and other perspective issues to a minimum). Preferably, this means within a few cm (5.0 cm, preferably less than 4.0 cm or less than 3.0 cm) from each other. The two imagers are azimuthally oriented substantially the same, i.e. are oriented in the same or almost the same vertical plane, but have different polar angles (i.e. are angled more upward or more downward in view of each other).

It should be noted that the orientation of the imagers to substantially overlap (in a central zone), has the further advantage that each imager separately can still provide a view for an operator or user of a focus zone. For instance, while each imager may have a focus orientation (up or down), both will still display the zone straight in front of the user. Said zone tends to be of interest in most cases, so the fact that this zone is in both imagers their field of view is especially convenient.

In a preferred embodiment, the HMD comprises one or more displays visible to the user when the HMD is worn, wherein the display is configured for displaying images from the first imager, images from the second images or aggregated images from the first and second imagers, wherein said aggregated images are created by combining images from the first and second imager into a single, aggregated image.

It should be understood that the display of may also be able to display images from other sources, such as an external imaging device, or video or photo data from external devices, which are connected to the HMD.

It should be understood that the HMD may or may not be a pair of smart glasses. In such a case, the HMD mentioned above, is the front frame of the smart glasses. In alternative versions, the HMD is a modular tool, and not necessarily a pair of smart glasses, and can potentially be removably connected to a pair of smart glasses, but similarly to regular glasses, or other headwear such as helmets, hard hats, and even caps.

As shown in the figures, the goal of the invention is to provide for a vertically elongate field of view, composed of the images from the two separate imagers, which are combined, and which can be displayed (on the display of the HMD and/or remotely), either in part or fully. This allows a user to focus on two zones of interest at ones, a first via his normal vision, and a second via the HMD or other display, which can show another area.

As mentioned, the HMD comprises an orientation determination means, preferably a gyroscope and/or an accelerometer and/or a magnetometer, for determining the orientations of the imagers. This can for instance be achieved by determining the relative vertical position of the first and second imagers with respect to each other, and with the pre-established knowledge of the relative orientation of the imagers. By being able to detect how the device is worn, in the first or second mode (thus determining which imager is facing upward), the input by a user (remote and/or wearer) for manipulating the display contents and/or images can be suitably converted according to the new reference frame, as well as what is displayed. This allows the device to be worn in two orientations, and allows a display, if present, to be positioned in front of the desired eye of the wearer.

In a preferred embodiment, the field of view of the imagers is substantially oblong, and the (field of view of the) imagers (is) are oriented in portrait mode, with the long sides of the oblong field of view being substantially vertical or perpendicular to the transverse plane.

The invention at hand is further aimed at solving an issue that is common with many HMD's with cameras and displaying capabilities. Most imagers that are used in HMD's are provided in landscape mode (i.e. with the width of captured images being higher than the width), as this matches the display used in such devices, which is also set in landscape mode. In order to maximize the use of the display, the imagers are therefore oriented in the same way, creating the effect of the image from the imagers being essentially forwarded to the display. However, in many applications, the operator (be it the wearer of the HMD or a remote operator) is not interested in a wide-angle view in the horizontal plane (especially for the wearer, who typically already relies on his vision for this). When studied further, the applicant notes that most of the operations and interactions lie in a narrow vertical zone, essentially straight in front of the operator wearing the headset. This can be picking up certain objects, working on an object or person lying in front of him or her, operating objects straight in front or slightly elevated. It is in these occasions that the operator wishes to maintain vision in a larger vertical zone in front of him, but does not have this capability due to the orientation and setup of the imagers on prior art systems. With the term "portrait mode", it is indicated that the oblong field of view of the imagers is oriented so that, when wearing the HMD under normal circumstances (standing up, looking forward), the longest dimension of the field of view is vertically oriented, and the shortest dimension is horizontally oriented. Even considering the option to turn the imager in portrait mode, to effectively widen the field of view in the vertical plane, in many cases this was still found to be insufficient.

Due to the portrait mode orientation of the imagers, the present invention is uniquely capable of displaying said central focus zone with both imagers, and at the same time also including an upper or lower zone in their field of view. Prior art systems employ landscape mode imagers, which would not be able to capture both zones, but in exchange provide a wider field of view which is the goal of said systems, which are sometimes employed with multiple cameras along the perimeter of the headset. However, such a wider field of view is of lower interest in certain applications as mentioned, and does not weight against the drawbacks in those cases.

In a further preferred embodiment, the device comprises a buffer wherein the images from the first and second imager are stored column per column before processing, and subsequently read out line by line from said buffer for further processing. Said buffer can be comprised within the portion of the device that is worn on the head of a user (typically the HMD), but may alternatively be comprised in an external device, which is wiredly (or wirelessly) connected to the HMD. Imagers are configured to write away their data row by row, thus creating a data matrix, in which the pixel data is stored. However, said imagers operate on the principle that they are oriented in landscape mode. By flipping the imager 90°, the images are in fact written away column by column physically speaking, but are interpreted to have been written away as physically row by row. However, in order for the images of the two imagers to be combined in an efficient fashion, access is necessary to the pixel data in a row by row format. Once the images are stored as such, it is highly inefficient to undo the process in order to regain the row by row pixel values. Therefore, instead of using a more complicated method of combining the images, which would increase the computational load, and thus require more advanced (expensive, voluminous and heavy) hardware as well as more battery power, as well as more time (creating lag on the image), the present invention uses a buffer to temporarily store the pixel data, from which buffer the data is subsequently retrieved column by column (which corresponds to the physical rows of the image), allowing a much easier recombination of the images into a single, aggregated image.

Having the buffer incorporated directly into the head worn section, means it can be placed proximate to the imagers, or even incorporated with them. Alternatively, placing the device in the pocket unit reduces energy consumption at the head worn section, and moves it to the pocket unit which houses the power supply, which is more efficient, but requires the image data to be transferred to the pocket unit before storage.

In a preferred embodiment, the first and second imager are rotationally fixed with respect to each other, preferably at least in the sagittal plane, more preferably also in the transverse plane (horizontally when wearing the device under normal conditions). Most preferably, the imagers are rotationally (as well as translationally) fixed to the HMD. Fixing the imagers with respect to each other eases operating conditions, as the combination of the images of the imagers need not be recalibrated entirely, which would be the case with 'movable' imagers. Having a preset and known alignment between the two, allows the processing unit to use preset combination parameters regarding relative position/orientation, strongly reducing energy consumption and computational taxation/requirements.

In a preferred embodiment, the images are processed for display on the HMD and/or on an external device in a first display mode associated to the first processing mode or in a second display modes associated to the second processing mode, said first and second display modes being essentially flipped or rotated with respect to each other, and preferably rotated over 180° with respect to each other. The term "flipped" preferably refers to a relative rotation of the two display modes over a certain angle around an axis perpendicular to the displayed image. For instance, in the first mode, the first imager is positioned above the second imager, while in the second mode this is reversed (or the other way around). The system operates under a standard, for instance that the first and second imagers are positioned correctly (not upside down) in the first mode, thereby not necessitating the reversal of the images when displayed or used at further stages. Likewise, this means that when the system detects the HMD to be worn in the second mode, it will be aware that the images acquired from the imagers will present an upside down view on the reality, allowing it to either process the images to be stored upside down, or annotated to be displayed upside down.

In a preferred embodiment, the first and second imagers are positioned in a central section of the HMD.

In certain embodiments, the HMD is adapted to be affixed to another piece of headgear, and are specifically adapted to be affixed in a central position with respect to the user's head, especially with elongate HMDs which are meant to span substantially across the forehead of the user. It was found that for both the wearer as well as the remote operator, the most desirable operating conditions are those that approximate the actual vision of the wearer. For the wearer, it is clear that a matching visual via the imagers is desirable, as the wearer will not need to adjust to the different point of view. For the remote operator, it is also important to obtain a point of view as close to that of the wearer as well, as during coordination between wearer and remote operator, a good communication is crucial, which requires a strong match between point of view.

In a preferred embodiment, the head-mounted device is provided with an external portable electronic device, to which it is detachably wiredly connectable, said electronic device comprising a processing unit, wherein the imagers are configured to forward acquired image data to said processing unit, and wherein said processing unit is configured for processing the forwarded images from the imagers into the aggregated images, and for providing the processed images to the display.

By delegating a number of processing operations, and preferably as many as possible, the requirements for the head worn section are substantially lowered, which presents numerous advantages. Any components in the HMD section, increase the weight, which is one of the main consumer concerns. In order to be able to provide them in the HMD section, these components further require scaling down (both in weight and in volume), to keep the HMD section compact (and light), which increases the cost, and often creates other disadvantages (such as lower quality). Lastly, components in the HMD section require a power supply. In the present invention, power supply is placed in the portable electronic device (pocket unit), to lower the weight of the HMD section, as batteries tend to have significant weight, as well as heat generation. If more power is necessary at the HMD due to an overload of electronic components, more power transfer is necessary between HMD section and pocket unit, which creates losses and may also require more advanced power supply cables between the two, but also creates more heat generation at the HMD section. By performing (most) processing actions at the pocket unit, power supply is optimized, weight and heat generation is reduced at the head worn section. Lastly, by forwarding the data before processing, it, data transfer is reduced as only the (generally) raw data is transferred, and not several processed versions thereof.

In a further preferred embodiment, the field of view of the imagers is oriented in portrait mode, with the long sides of the field of view being vertical or perpendicular to the transverse plane, and wherein the images from the first and second imager are stored column per column before processing, and subsequently read out line by line from said buffer for further processing, and wherein the buffer is comprised in the external portable device. The advantages of the foregoing has been discussed previously.

In a further preferred embodiment, the processing unit is adapted to forward a section in landscape mode of the aggregated image for being displayed on the display, wherein the section is cropped from the aggregated image based on instructions from a remote user communicating with the processing unit and/or on instructions from a user wearing the head-mounted device via a portion of the head-mounted device that is worn on the head and/or via the external portable electronic device.

As mentioned, displays on HMD devices are typically provided in a landscape mode. As such, in order to take full advantage of it, the displayed image is generally also in landscape mode. However, in the present invention, the images of the two imagers are combined, creating a vertically elongated aggregated image (especially so in case of the imagers being oriented in portrait mode). Therefore, the display can only show a cropped section of the aggregated image. The choice of which section is displayed can be dynamic, and steered from either or all of a head-worn portion of the HMD, the pocket unit (portable electronic device) from the wearer's end, but can also or alternatively be controlled by a remote operator. Generally, it is preferred that both the wearer and the remote operator can adapt the cropped section.

The wearer can change the cropped section for display via an input system such as a touchpad, voice activation, or via head gestures measured by a gyroscope/accelerometer, hand gestures (optionally via another input mechanism, such as handheld tool). The user input system is preferably provided on a lateral side of the head worn portion, for instance at a temple zone of the portion in case of a HMD which stretches across a substantial portion of the forehead when worn (i.e., a zone proximate to the temple when the HMD is worn). Most preferably, the user input system faces laterally outward, away from the user as this allows easy manipulation and does not impugn upon the vision of the wearer.

A remote operator may have more options, such as providing input via a mouse, touchpad, touchscreen, keyboard, etc., but may also avail him to other input methods, such as voice control, hand and/or head gestures.

In some embodiments, the operator can (reversibly) lock out the control and/or input of the wearer. In some embodiments, the wearer can (reversibly) lock out the control and/or input of the remote operator. In certain embodiments, both can lock out each other's control and/or input, and reinstate each other's control and/or input.

In a preferred embodiment, a portion of the HMD that is worn on the head and/or the external portable electronic device comprise a user input system, preferably via a touch sensitive input surface, with which the processing unit can be provided with an input to switch between displaying the images acquired by the first imager, the images acquired by the second imager or the aggregated images. We refer to the previous paragraphs for further info on potential embodiments of the user input system.

In a similar embodiment, the HMD can be provided with a user input system (again potentially according to previously discussed embodiments) to change the displayed section of the aggregated image, or in the images of the first and second images (for instance, scrolling up, down or even sideways in the aggregate image; in some embodiments, zooming in and/or out can also be enabled).

In a preferred embodiment, the head-mounted device is adapted to be attached to a carrier via the HMD, said carrier to be worn on the head of a user (most preferably wherein the head-mounted device does not comprise temples). In a specifically preferred embodiment, the HMD relates to a compact module, which can be attached laterally to the headwear, or alternatively in a hanging position. The advantages, as discussed previously and further on, is that the orientation determination means and the two imagers which face in different directions, but preferably (largely) symmetrically in view of the transverse plane, allow the HMD to be attached at both sides (left and right) for a user, by simply rotating the device. The device then can adapt to the changed orientation on its own, and process the captured images automatically.

Preferably, the HMD comprises a display which is movably connected to the HMD, and the display can be moved to a first position at a first side of the HMD and to a second position at a second side of the HMD, said second side opposite to the first side, wherein in both the first and the second position the display is facing towards the user wearing the head-mounted device.

The display may be moved between the two positions in a number of fashions, for instance via a translation, or via a rotation around one or more axes (single rotation around an axis extending straight ahead away from the user; double rotation around two horizontal axes perpendicular to an axis extending straight ahead away from the user to ensure the display is facing the user again; or other variations).

The system is configured (if necessary) to recognize how the display is facing (whether it has 'flipped', switching which sides are up and down), and to adapt the mode of display of the image to fit the orientation of the display.

The above embodiment has the advantageous feature that it can be clipped onto another headset, a helmet or hat (for instance a hard hat), a cap, or other headgear, preferably via a brim, for any user. About 70% of the population are right-eye dominant, with the other 30% being left-eye dominant (ocular dominance, eye preference or eyedness), and prefer visual input from a particular eye over the other. Furthermore, research has shown that dominance can change and may switch between the eyes depending on the task at hand, and the physical condition of the subject (for instance, fatigue). It is therefore advantageous to provide for a head-mounted device that can be attached to a carrier in both ways, allowing it to be flipped so the display faces the desired eye. Not only is this convenient for a user, who is guaranteed that the device will match his 'eyedness' and can even be flipped during use depending on task or physical condition, but it is also advantageous as a single HMD will be sufficient in cases where the user will vary, instead of two sets of HMD's (a left and a right version). By adapting the display to be movable between a first and a second position (which are at opposite sides of the HMD in view of each other, either at opposite sides of the transverse plane, or on opposite sides of the sagittal plane), it can be ensured that simply rotating the HMD (around an axis extending straight away from the user when wearing the HMD) over 180°, the imagers in the HMD (which are typically positioned centrally) will still face forward (and substantially in the same position as before).

It can be understood that, in order to allow the HMD to be used in a first orientation and a second orientation (flipped), it is important that the first and second imagers are positioned symmetrically with respect to each other. This means that, if the first imager is facing upward under an angle of X° with respect to the horizontal plane, when the user wearing the device is facing straight ahead, then the second imager is facing downward under essentially the same angle of X° (or –X°) with respect to the horizontal plane. When reversed, the second imager will be facing upwards under the angle of X°, and the first imager will be facing downward under angle of X° (or –X°).

Additionally, many prior art systems use cameras that are fixed to a lateral side of the head set, as this can allow some variation in its tilting angle, but mainly as such an imager is not (or less) limited in volume restrictions. However, in these cases, the software processing the camera images takes into account the lateral position of the camera, and adapts and accounts (in part) for the lateral shift of the camera in view of the wearers vision. If such a camera is flipped, then this adaptation needs to be reversed and applied for the other lateral position. In the present invention, the imagers are positioned essentially central in the HMD (i.e., between the eyes of the user), thus creating (virtually) no offset of the imager positions between one mode of wearing, and the other flipped mode.

In a further preferred embodiment, the HMD comprises a removable connection means, the HMD comprising a first mounting means at a first face of the HMD, and the HMD comprising an second mounting means at a second face of the HMD, said second face being opposite to the first face, said first and second mounting means being configured for the connection means to be removable attached thereto (for instance via screws, clamps, or other means), said connection means being adapted for removable connection to headwear, preferably to a helmet or hard hat, more preferably to the bottom surface of a brim of the hard hat or helmet, or alternatively to lateral sides of such headwear, also including headsets, glasses (smart and regular). The connection means can be adapted to function/interact/interface with specific connectors on the headwear, or can be adapted to function generally (for instance, with clamping or other connecting systems that can be repositioned to adjust to different-size headwear). Preferably, said first and second face are at the lateral sides of the HMD, allowing the HMD to be connected at the temple side to another piece of headgear, such as a helmet, glasses or others. In another preferred embodiment, the first and second face are at the top and bottom sides, allowing connection to the brim.

In a preferred embodiment, the overlapping field of view of the first and second imagers is centered around a polar angle of about 0°. This ensures the 'shared' region of both imagers is straight ahead of the user, and is the object of his or her focus.

In a preferred embodiment, the aggregated field of view has a total angle originating from the HMD of at least 100°, preferably at least 110°, more preferably at least 120°, in the sagittal plane. One of the goals in the present invention, is to provide for solutions in which the user has an interest in a vertically extending region in front of him or her. This can be the case for instance during surgery, where the surgeon will be focused on his or her hands (downward), and from time to time needs to review certain aspects or statistics or other information on monitors which typically hang over-head (upwards). As such, it is crucial that a vertically extended field of view can be achieved at all times, which is accomplished by combining the two imager field of views, each of which already have their longest dimension along the vertical axis. Another such application is in order-picking, where an operator usually is interested in what is right in front of them, and what is above them.

In a preferred embodiment, the aggregated field of view has a total angle originating from the HMD of at least 70°, preferably at least 80°, in the transverse plane.

In a preferred embodiment, the imagers are located at the forward facing side, wherein the first imager is angled at an upward polar angle between 10° and 30°, preferably at least 15° or 20°, and wherein the second imager is angled at a downward polar angle between 10° and 30°, preferably at least 15° or 20°. As mentioned previously, it is the intention to provide for a horizontally symmetric HMD (in terms imagers, and preferably also in terms of connection options to headwear), so that, when rotated to an extent that the top and bottom side of the HMD are switched, the imagers are essentially mirrored onto each other, and thereby provide for the same field of view upwards and downwards, allowing the user to wear the display at the left and right side, depending on situation and/or user preference.

In a preferred embodiment, the HMD is provided with a cushioning section at the back face (facing the user's head) to provide for a comfortable wearing experience.

In a preferred embodiment, a rotation stopper is provided, preferably at the lateral side of the HMD where the arm of the display is connected. This stopper extends from the frame in order to limit the rotation range of the arm up to a certain point, and can function as a resting position for the arm in which the display is provided at a suitable distance from the eye of a user. The stopper can limit the rotation in both directions, thereby ensuring a suitable position (distance from the eyes) both in the first and second position of the display. In some embodiments, the stopper can however be an internal mechanism delimiting the rotation of the hinges.

In a preferred embodiment, the first and second imager are positioned fixedly with respect to each other, to prevent shifting in position or angulation which would require frequent recalibration or constant adaptation when combining the images. Preferably, the imagers are fixed in a holding assembly in an imager module, whereby the holding assembly comprises a temperature-resistant material (linear thermal expansion coefficient below $250 \cdot 10^{-5}$ per Kelvin, such as acrylonitrile butadiene styrene (ABS), or even glass reinforced ABS) to ensure minimal deformation under temperature variation, thus ensuring angular and positional stability between the two imagers.

In a preferred embodiment, the HMD is a compact module (i.e. not longitudinal) that can be added onto existing headwear, such as headsets, (regular or smart) glasses, helmets, caps, etc., preferably at a lateral position. This can be enabled via a simple connection system, a strap, a screw, velcro, or other means. Such a device would provide for an extremely beneficial modular 'upgrade', that can be attached to even more diverse types of headwear.

In such an embodiment, the shape of the module can vary. In an embodiment, the shape is elongate, to allow multiple connections elements for fixing the module to headwear at a number of positions along the length, to ensure stability. This would be especially convenient to mount the module to temple sections of headwear or other sections of headwear that traverse along the side of the head when worn. The stable fixation to the headwear is crucial as it is the intention to hold the imagers steady, as well as the display. Therefore, multiple connection elements are preferred. These can be straps which can be adjusted for varying breadths and widths of the sections to/around which it is to be attached, but various other options can be imagined. However, for certain types of headwear, a single connection element can be sufficient, if it can be fixed to block relative rotation or other movements.

In this embodiment, the HMD module may comprise one or more of the components mentioned in any one of the embodiments above, with at least the one or more displays and the two imagers with overlapping field of view, under the same restrictions as mentioned for the first aspect. It should be clear that the first and second imagers again are positioned under different angles with respect to each other, with a plane of symmetry being defined by the two fields of view (the field of view of the first imager being X % at one side of plane of symmetry, with the second imager's field of view being X % at the other side of the plane of symmetry). For interpretation of the above, the plane of symmetry can be understood to represent the horizontal plane.

Again, the imagers are preferably oriented in portrait mode to enable aggregated images which have a much longer field of view in the vertical sense.

The field of view of both imagers is substantially centered according to a shared direction (i.e. the first and second imagers having a first and a second longitudinal symmetry axis that are substantially parallel to each other, and a first and second 'short' symmetry axis that are substantially parallel to each other). Preferably, the longitudinal axes approximately overlap each other, which means the imagers provide images which lie in each other's extension along their longest dimension (creating the desired 'long' vertical image). It is in this sense that the 'longitudinal direction' of the HMD will be parallel with one of the symmetry axes (either the longitudinal or the short, depending on the orientation of the imagers, but preferably the short symmetry axes when the imagers are stacked in portrait mode).

Preferably, the module has a maximal width (i.e. the breadth of the module perpendicular to the plane defined by the lines of vision of the two imagers (corresponding to perpendicular to the sagittal plane) of at most 12.0 or 10.0 cm, preferably at most 9.0 cm, more preferably at most 8.0 cm, even more preferably at most 7.0 cm, or even less such as 6.0 cm, or 5.0 cm at most. It is advantageous to limit this dimension as this can be a length over which the module extends from the head when worn along the side.

Preferably, the two imagers are positioned in a single plane parallel to the sagittal plane (with their orientations also extending in/parallel to said single plane).

Preferably, the module comprises the two imagers, a touchpad (or similar input system), display, a microphone, a speaker.

Preferably, the display is movable with respect to the module itself, preferably via one or more hinges as discussed, to allow placement of the module at the left and right side of the headwear (for left- or right-eyed users). Allowing the module to be moved and reoriented, it is ensured that in each case, the display can be provided at eye level and in the correct orientation. In fact, in the present version, the display can be moved more easily to be correctly positioned, via a single rotatable connection between an arm for the display and the module itself, or even without requiring rotation for a module compatible with glasses, as the attachment point for the module to the glasses is at eye height, so the display can be positioned in front of the eye by an arm which places the display at the same height position as the module. By rotating the module over 180° around a sagittal axis (straight ahead), it can be connected to the other side of the glasses, with the arm again positioning the display at eye height.

Preferably, the variation is further adapted according to one or more of the foregoing embodiments.

Alternatively, the module can be attached on both sides with the same side facing upwards, and is essentially rotated over 180° around a vertical axis, thereby allowing connection via the same connection elements, wherein the arm supporting the display will need to be rotated over one or more axes (or optionally, the display being rotatable in view of the arm itself) to be provided in front of the eyes of the wearer, depending on the build of the device.

Another version can allow attachment of the module to a headwear, at two opposite sides of the module. This way, the carrier (and optionally also the display) will need to be rotated over one or more axes to be provided in front of the eyes of the wearer again.

Further incorporations of the preferred embodiments of the first aspect of the invention in to the variation are preferable as well, such as a buffer being comprised in the module wherein the images from the first and second imager are stored column per column before processing, and subsequently read out line by line from said buffer for further processing, preferably wherein the buffer is comprised in the headset. Other further embodiments, such as a user input system (touchpad or the likes), specific connection and/or connection means as discussed previously, are preferably included as well.

In a possible embodiment, the HMD is longitudinal, and extends parallel to the transverse plane and perpendicular to the sagittal plane.

In a preferred embodiment, the HMD houses a number of electronic components, but is preferably kept compact. The length (dimension along the longitudinal axis) typically matches the breadth or width of a human head, and is in a range between 130 mm and 240 mm, preferably between 150 mm and 230 mm, more preferably between 170 and 220 mm, and most preferably around 190 to 210 mm. The height should be kept as low as possible to avoid impugning the wearer's vision, and is preferably ranged between 10 mm and 50 mm, preferably between 15 mm and 35 mm, more preferably between 17.5 mm and 25 mm. The thickness (distance between front and back face of the HMD) is preferably also kept low, and is ranged between 10 mm and 70 mm, preferably between 20 mm and 60 mm, more preferably between 30 mm and 55 mm. We note that the thickness can vary over the length of the device, as it is preferably curved to (partly) follow the curvature of the human forehead. This may allow the thickness to increase away from the central region, where it is kept lowest (preferably at most 40 mm, and more preferably at most 35 mm), towards the lateral ends where it may be higher (preferably at most 70 mm, more preferably at most 60 mm). These dimensions allow the HMD to be voluminous enough to allow the components to be comprised therein, while balancing performance, cost and other factors, such as heat generation, power requirements and others.

As mentioned, one of the secondary goals of the invention is to keep the HMD as light as possible by moving components to an external device as much as possible. However, for some components, it is either necessary or advantageous to keep them in the HMD. The electronic components housed in the HMD may comprise one or more of the following: a field-programmable gate array (FPGA), an audio digital signal processor (audio DSP), an accelerometer (most preferably kept in the HMD), one or more connectors (plug) for receiving cable connectors (jacks), a double data rate (DDR) random-access memory (RAM) component (or preferably DDR synchronous dynamic (SD)RAM), or other components, such as a gyroscope, a CPU, a compass. The skilled person will recognize that one or more of the above components may be provided in the external portable device to reduce weight and volume of the HMD.

Of course, it may also be envisioned that one imager is in portrait mode (both here as well as for the original invention), while the other imager is in landscape mode. However, the skilled person will, in view of the present document, be able to implement the teachings to such an embodiment as well.

In a further aspect, the invention relates to the use of a head-mounted device according to the first aspect during surgery.

In another further aspect, the invention relates to the use of a head-mounted device according to the first aspect during order-picking.

In another further aspect, the invention relates to the use of a head-mounted device according to the first aspect during remote assistance.

However, it is obvious that the invention is not limited to the above applications.

The present invention will be now described in more details, referring to examples that are not limitative.

EXAMPLES AND DESCRIPTION OF FIGURES

Example 1

Figures 2A, 2B:
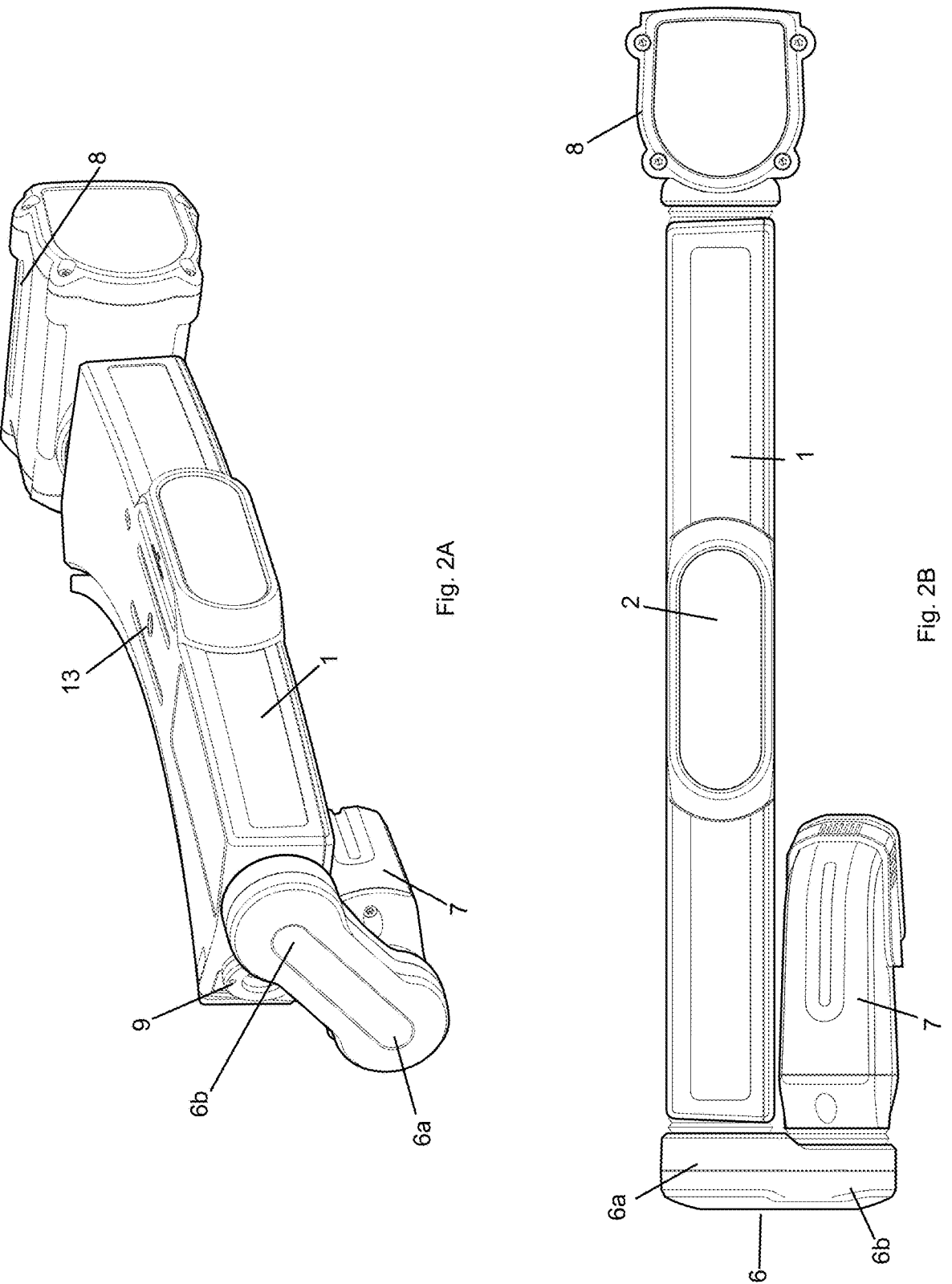
FIG. 2A-B show a different perspective view of a HMD according to an embodiment of the invention, without (2A) and with (26) a connection means attached to the HMD.

FIGS. 1A-B and 2A-B show a HMD (1) according to the invention. In the present Figures, further options are displayed which the skilled person will recognize as optional features, such as a lateral camera module (8) comprising a tertiary imager (which in some embodiments may be a variable-focus imager), which may be fixedly or removably attached to the HMD (1), and preferably is rotatably connected to allow variation of the angle of the lateral camera module (8) with respect to the rest of the HMD (1). Typically, this variation is established through rotation around an axis extending along the HMD to allow tilting of the camera, but the connection between the two may also allow rotation around other axes, for instance via a ball-and-socket joint or similar structures. FIGS. 16 and 2B also disclose a speaker (3) positioned centrally, which can be positioned elsewhere, or can even be wholly absent. It is clear that such features are not essential to the present invention and can in no way be construed as obligatory.

FIGS. 1A-B and 2A-B show a HMD (1), which extends essentially along a longitudinal axis. In preferred embodiments, the HMD is slightly curved (as can be seen on FIGS. 1A and 2A) to better approximate the curvature of a wearers head, to increase user comfort. In some embodiments, the curvature is only present at the back side (user-facing side) of the HMD, in others, the HMD has a monotonous thickness (distance between front and back face of HMD).

In a central region of the HMD (1), an imager module (2) is present, comprising a first (2*a*) and a second (2*b*) imager (as can be seen in FIGS. 16 and 2B), the former facing slightly upward, the latter facing slightly downward. The two imagers (2*a*, 2*b*) are positioned at a substantially similar vertical position ('elevation'), so the height from which they over a point of view strongly matches. Additionally, the imagers (2*a*, 2*b*) are positioned as close to each other horizontally as well, further ensuring that the images can be combined easily, with little side-effects from the offset in horizontal position, and with minimal parallax to account for.

It is in this sense that the imagers are positioned fixedly with respect to each other, to prevent shifting in position or angulation which would require frequent recalibration or constant adaptation when combining the images. The imagers (2*a*, 2*b*) are preferably fixed in a holding assembly in the imager module (2).

A display (7) is towards one lateral side of the HMD (1), in order for the display (7) to be facing the eye of a user wearing the HMD. The display is provided on a double-hinged arm (6), which is attached to a lateral side of the HMD via a first rotatable connection (6*a*), and to which arm (6) the display (7) is rotatably attached via a second rotatable connection (6*b*). The rotatable connections (6*a*, 6*b*) allow rotation around two substantially parallel axes, which generally extend along the longitudinal axis of the HMD. The first rotatable connection (6*a*) allows the display to be positioned in a first position beneath (while being worn normally) the HMD (1), and in a second position above (again, while being worn normally) the HMD (1). The second rotatable connection (6*b*) allows the display (7) to be rotated in order to face the user when switching between the first and second position. As discussed, this allows users to 'flip' or rotate the HMD in order to change the position of the display between the left or right eye.

The HMD (1) comprises a first mounting means (13) at the top side of the HMD (1), to which in the FIG. 1A-B a removable connection means (4) is attached, in this case via a screw (5), although other connection elements or techniques can be easily envisioned (snap-fit, velcro, clasp, etc.). A similar mounting means is provided at the opposite side (bottom side) of the HMD (1), which allows the connection means to be mounted at both sides in order to enable attachment to another structure in a first orientation, and in a second orientation, rotated over 180° around a horizontal axis with respect to the first orientation, in order to be suitable for left-eyed and right-eyed wearers (and/or specific conditions). The connection means (4) is configured to be couplable to a matching connection means on a head-worn carrier (or couplable directly to the carrier), such as a hard hat, cap or other pieces of headwear. In particular, helmets, hard hats and caps provide for excellent carriers as the horizontal brim provides for a perfect connection point. Again, the connection means may be coupled to the carrier's connection means via a range of options, such as snap-fit, velcro, clasps, etc.

A plug or connector (9) for receiving cables is provided at a lateral side of the HMD, this way avoiding to be in the way of the user.

Figure 3:
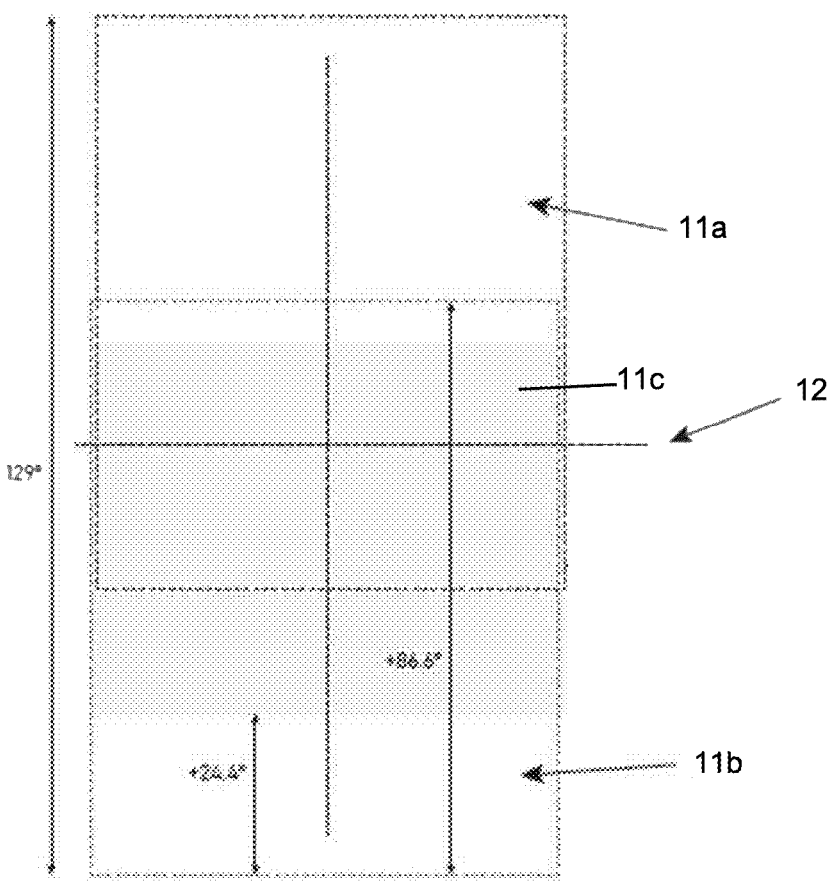
FIG. 3 shows a visualization of the field of view of the first and second imagers, and the aggregated field of view, according to an embodiment of the invention, compared against the field of view of a prior art HMD device with single imager.

FIG. 3 shows the fields of view of wide-angle first and second imagers in portrait mode, and their aggregated field of view. As can be seen, the field of view (11*a*) of the first imager (2*a*) is slightly elevated with respect to the horizon (12), and the field of view (11*b*) of the second imager (2*b*) is slightly lower with respect to the horizon (12), preferably to the same extent (same angle with respect to the horizontal plane). For illustration purposes, the field of view (13) of a 'normal' imager typically used in HMD's, in landscape mode, is shown. As can be seen, a section (11*c*) of the fields of view (11*a*, 11*b*) of the two imagers overlaps, and this overlapping section (11*c*) is vertically centered around the horizon (12). The total field of view in the FIG. 3 has a vertical angle of about 129°, although this can be varied by increasing or decreasing the overlapping section (11*c*). The separate imagers have a field of view with a vertical angle of about 86.6°, which again varies depending on type of imager, and can thus be accommodated to circumstances. In FIG. 3, the overlapping section (11c) of the field of view thus has a vertical angle of about 44.2°.

Example 2

Figure 4A:
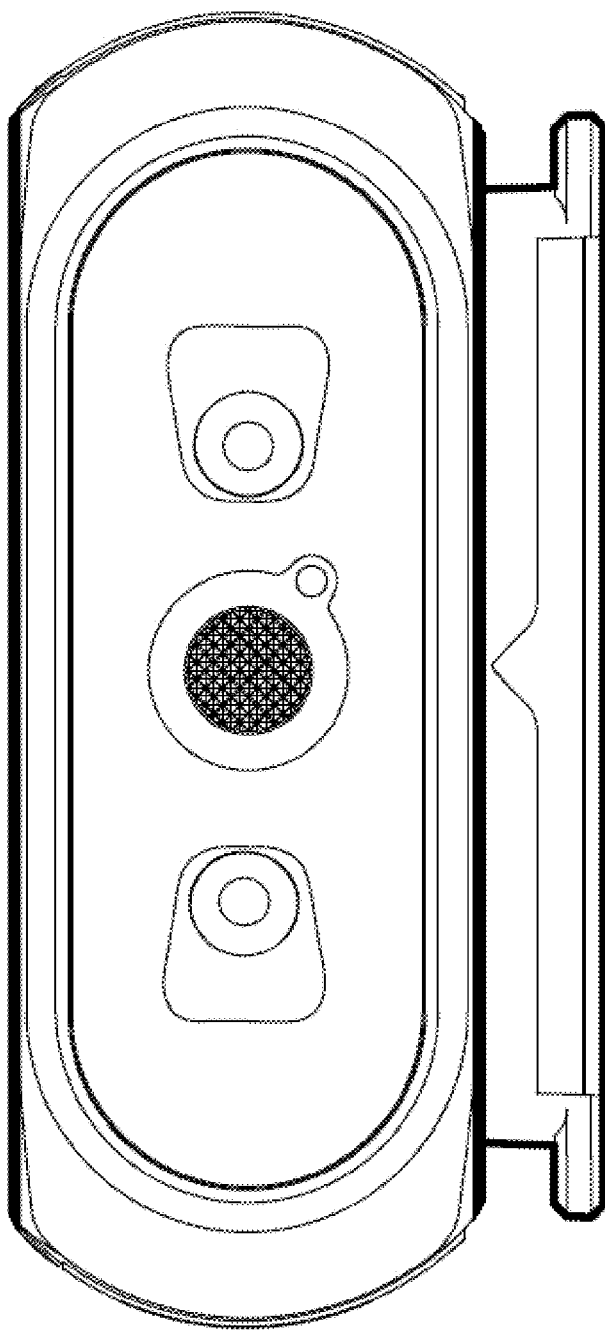
FIG. 4A-B show a frontal view of a HMD according to an embodiment of the invention, FIG. 4A with a single connection means, FIG. 46 with a double connection means.

FIGS. 4A and 46 show a frontal view of a more compact embodiment of the HMD according to the invention, adapted to be worn (preferably along the side) on headwear, preferably connected to the temple section. In the embodiment, the two imagers (2a, 2b) have a line of vision which essentially diverge, with the lower imager (2b) being tilted downwards, and the upper (2aa upwards. In some embodiments this is reversed, with the lower imager (2b) being tilted upwards, and the upper downwards (2a) so the lines of vision cross each other.

Figure 4B:
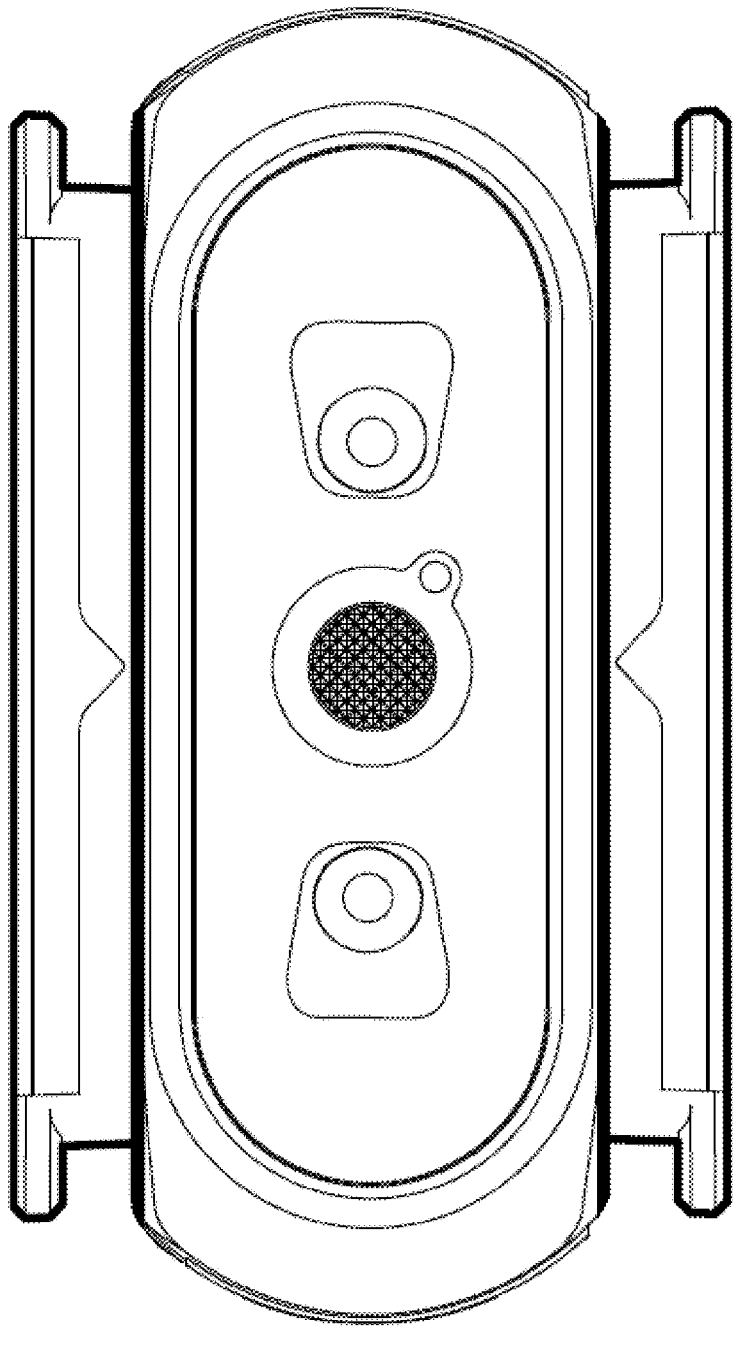

In the embodiment of FIG. 4A, a single connection means (4) is provided at a lateral side of the HMD (1) for connecting the HMD to a piece of headwear. The HMD (1) can still be connected to headwear at the left or right side thereof, but will require the HMD (1) to be rotated over 180°. In the embodiment of FIG. 46, connection means (4) are provided at both lateral sides to allow coupling at both sides of the HMD (1) without necessarily requiring rotation of the HMD. In this version, it can be understood that the orientation determination means are not strictly necessary. In the version of FIGS. 4A-B, a speaker (3) is also provided, though this is merely optional.

It should be noted that the imagers can also be positioned along each other's side, though this will typically make the module less compact (extending further away from the head when worn along the sides).

The invention claimed is:

1. Head-mounted device (HMD) comprising at least two spatially separated imagers;

said HMD further comprising a front side and a back side, a top side and a bottom side divided by a transverse plane, and two lateral sides divided by a sagittal plane, wherein said transverse plane is essentially horizontal and said sagittal plane is essentially vertical and perpendicular to the transverse plane when the HMD is worn by a forward-facing user holding their head straight;

wherein the imagers are oriented under a different polar angle, the polar angle being thean angle of the perpendicular projection of the orientation of the imagers onto the sagittal plane with respect to the transverse plane;

wherein the orientations of the first imager and the second imager define an angle of at least 15°;

wherein the imagers are oriented under a substantially similar azimuthal angle, the azimuthal angle of the imagers being the angle of the perpendicular projection of the orientation of the imagers onto the transverse plane with respect to the sagittal plane, whereby said azimuthal angles are between −15° and +15°;

wherein the orientations of the first imager and the second imager extend into different half spaces defined by the transverse plane;

and wherein the field of view of the imagers is partially but not entirely overlapping, whereby no greater than 70% of the aggregated field of view of the two imagers being an overlapping field of view of the imagers;

wherein the overlapping field of view has an angle of at least 20°, in the sagittal plane originating from a center point between the imagers;

wherein the imagers are positioned within less than 5.0 cm from each other;

wherein the HMD is further provided with a carrier to be worn on the head of the user, and the HMD is attachable to the carrier in the first mode with the top side facing up and the bottom side facing down, and in the second mode with the top side facing down and the bottom side facing up when the user wearing the carrier on their head is facing forwards;

wherein said HMD can be worn in a first mode with the top side facing up and the bottom side facing down, and in a second mode with the top side facing down and the bottom side facing up;

wherein the HMD comprises an orientation determination means selected from the group consisting of a gyroscope, an accelerometer, a magnetometer, or combinations thereof, for determining whether the HMD is worn in the first or second mode, thereby determining the orientation of the first and second imagers;

wherein the device is configured to, based on said determined mode wherein the HMD is worn and/or the orientation, process the images in a first processing mode or in a second processing mode.

2. The head-mounted device according to claim 1, wherein the carrier is headwear.

3. The head-mounted device according to claim 1, wherein the HMD comprises a connection means at the top side and at the bottom side, said connection means being suitable for mounting the HMD on a connector on the carrier.

4. The head-mounted device according to claim 1, wherein the HMD comprises one or more displays visible to the user when the HMD is worn, wherein the display is configured for displaying images from the first imager, images from the second images or aggregated images from the first and second imagers, wherein said aggregated images are created by combining images from the first and second imager into a single, aggregated image.

5. The head-mounted device according to claim 1, wherein the field of view of the imagers is substantially oblong, and wherein the imagers are oriented in portrait mode, with the long sides of the field of view being substantially vertical.

6. The head-mounted device according to claim 5, further comprising a buffer wherein the images from the first and second imager are stored column per column before processing, and subsequently read out line by line from said buffer for further processing, wherein the buffer is comprised in the headset.

7. The head-mounted device according to claim 1, wherein the first and second imager are rotationally fixed with respect to each other at least in the sagittal plane; and wherein the first and second imager are rotationally fixed in the HMD.

8. The head-mounted device according to claim 1, wherein the device is configured to process images for display on the HMD and/or on an external device in a first display mode associated to the first processing mode or in a second display modes associated to the second processing mode, said first and second display modes being essentially flipped with respect to each other, and rotated over 180° with respect to each other.

9. The head-mounted device according to claim 1, wherein the first and second imagers are positioned in a central section of the HMD.

10. The head-mounted device according to claim 1, wherein the head-mounted device is provided with an external portable electronic device, to which it is detachably wiredly connectable, said electronic device comprising a processing unit, wherein the imagers are configured to forward acquired image data to said processing unit, and wherein said processing unit is configured for processing the forwarded images from the imagers into the aggregated images, and for providing the processed images to a display of the HMD wherein the carrier is headwear, and wherein the images from the first and second imager are stored column per column before processing, and subsequently read out line by line from said buffer for further processing, and wherein the buffer is comprised in the external portable device.

11. The head-mounted device according to claim 10, wherein the processing unit is adapted to forward a section in landscape mode of the aggregated image for being displayed on the display, wherein the section is cropped from the aggregated image based on instructions from a remote user communicating with the processing unit and/or on instructions from a user wearing the head-mounted device via a portion of the head-mounted device that is worn on the head and/or via the external portable electronic device.

12. The head-mounted device according to claim 1, wherein a portion of the HMD that is worn on the head and/or the external portable electronic device comprise a user input system comprising a touch sensitive input surface, with which the processing unit can be provided with an input to switch between displaying the images acquired by the first imager, the images acquired by the second imager or the aggregated images.

13. The head-mounted device according to claim 1, wherein the head-mounted device is adapted to be attached to a carrier via the HMD, said carrier to be worn on the head of a user, wherein the head-mounted device does not comprise temples; wherein a display is movably connected to the HMD, and wherein the display can be moved to a first position at a first side of the HMD and to a second position at a second side of the HMD, said second side being opposite to the first side, wherein in both the first and the second position the display is facing towards the user wearing the head-mounted device.

14. The head-mounted device according to claim 13, wherein the HMD comprises a removable connection means, the HMD comprising a first mounting means at a first face of the HMD, and the HMD comprising an second mounting means at a second face of the HMD, said first and second sides being oppositely positioned, said first and second mounting means being configured for the connection means to be removable attached thereto, said connection means being adapted for removable connection to headwear.

15. The head-mounted device according to claim 1, wherein the overlapping field of view of the first and second imagers is centered around a polar angle of about 0°.

16. The head-mounted device according to claim 1, wherein the aggregated field of view has a total angle originating from the HMD of at least 100° in the sagittal plane.

17. The head-mounted device according to claim 1, wherein the HMD comprises a forward facing side, a user facing side opposite to the forward facing side, an upward facing side, and a downward facing side opposite to the upward facing side, wherein the imagers are located at the forward facing side, wherein the first imager is angled at an upward polar angle between 10° and 30° with respect to an axis traversing the forward and user facing side of the HMD, and wherein the second imager is angled at a downward polar angle between 10° and 30° with respect to an axis traversing the forward and user facing side of the HMD.

* * * * *